US00PP21684P2

(12) United States Plant Patent
Danziger

(10) Patent No.: US PP21,684 P2
(45) Date of Patent: Jan. 25, 2011

(54) ***SUTERA* PLANT NAMED 'DANCOP29'**
(50) Latin Name: *Sutera cordata*
Varietal Denomination: DANCOP29

(76) Inventor: Gabriel Danziger, PO Box 24, Moshav Mishmar Hashiva, Beit Dagan (IL) 50297

( * ) Notice: Subject to any disclaimer, the term of this patent is extended or adjusted under 35 U.S.C. 154(b) by 0 days.

(21) Appl. No.: 12/383,772

(22) Filed: Mar. 27, 2009

(51) Int. Cl.
*A01H 5/00* (2006.01)

(52) U.S. Cl. ..... Plt./485
(58) Field of Classification Search ..... Plt./485

See application file for complete search history.

*Primary Examiner*—June Hwu

(57) ABSTRACT

A new and distinct *Sutera* cultivar named 'DANCOP29' is disclosed, characterized by a trailing growth habit, very well branched plant, large flower size and vigorous growth. The new variety is a Sutera, normally produced as an outdoor garden or container plant.

2 Drawing Sheets

Latin name of the genus and species: *Sutera cordata.*
Variety denomination: 'DANCOP29'.

BACKGROUND OF THE INVENTION

The new *Sutera* cultivar is a product of a planned breeding program conducted by the inventor, Gabriel Danziger, in Moshav Mishmar Hashiva, Israel. The objective of the breeding program was to produce new varieties of *Sutera* for commercial introduction. The seed parent is the unpatented, proprietary seedling variety referred to as *Sutera cordata* 'CV-05-150.' The pollen parent is an unknown *Sutera cordata* variety, as the new variety is the result of an open pollination in which the male parent cannot be identified. The crossing was performed May 2005. The new variety was discovered in February 2006 by the inventor in a group of seedlings resulting from the crossing, in a commercial greenhouse in Moshav Mishmar Hashiva, Israel.

Asexual reproduction of the new cultivar 'DANCOP29' by vegetative cuttings was first performed at a commercial greenhouse in Moshav Mishmar Hashiva, Israel in March 2006. Subsequent propagation has shown that the unique features of this cultivar are stable and reproduced true to type on successive generations.

SUMMARY OF THE INVENTION

The cultivar 'DANCOP29' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANCOP29.' These characteristics in combination distinguish 'DANCOP29' as a new and distinct *Sutera* cultivar:

1. Trailing growth habit.
2. Very branched, elongated plant.
3. Large flower size.
4. Blue flower color.
5. Vigorous plant.

PARENTAL COMPARISON

Plants of the new cultivar 'DANCOP29' are similar to plants of the seed parent, *Sutera cordata* 'CV-05-150' in most horticultural characteristics, however, plants of the new cultivar 'DANCOP29' have a more trailing growth habit, larger flower, different flower color and a faster, more vigorous growth habit.

COMMERCIAL COMPARISON

Plants of the new cultivar 'DANCOP29' can be compared to the commercial variety 'DANGUL14,' U.S. Plant Pat. No. 18,194. Plants of 'DANCOP29' are similar to plants of 'DANGUL14' in most horticultural characteristics, however, plants of the new variety are have a more trailing plant habit, smaller flowers, different flower color and a faster, more vigorous growth habit.

Plants of the new cultivar 'DANCOP29' can also be compared to the commercial variety 'DANCOP21,' U.S. Plant Pat. No. 19,349. Plants of 'DANCOP29' are similar to plants of 'DANCOP21' in most horticultural characteristics, however, plants of the new variety are have a more trailing plant habit, better branching, slightly larger flowers, and a faster, more vigorous growth habit.

BRIEF DESCRIPTION OF THE PHOTOGRAPH

Figure 1:
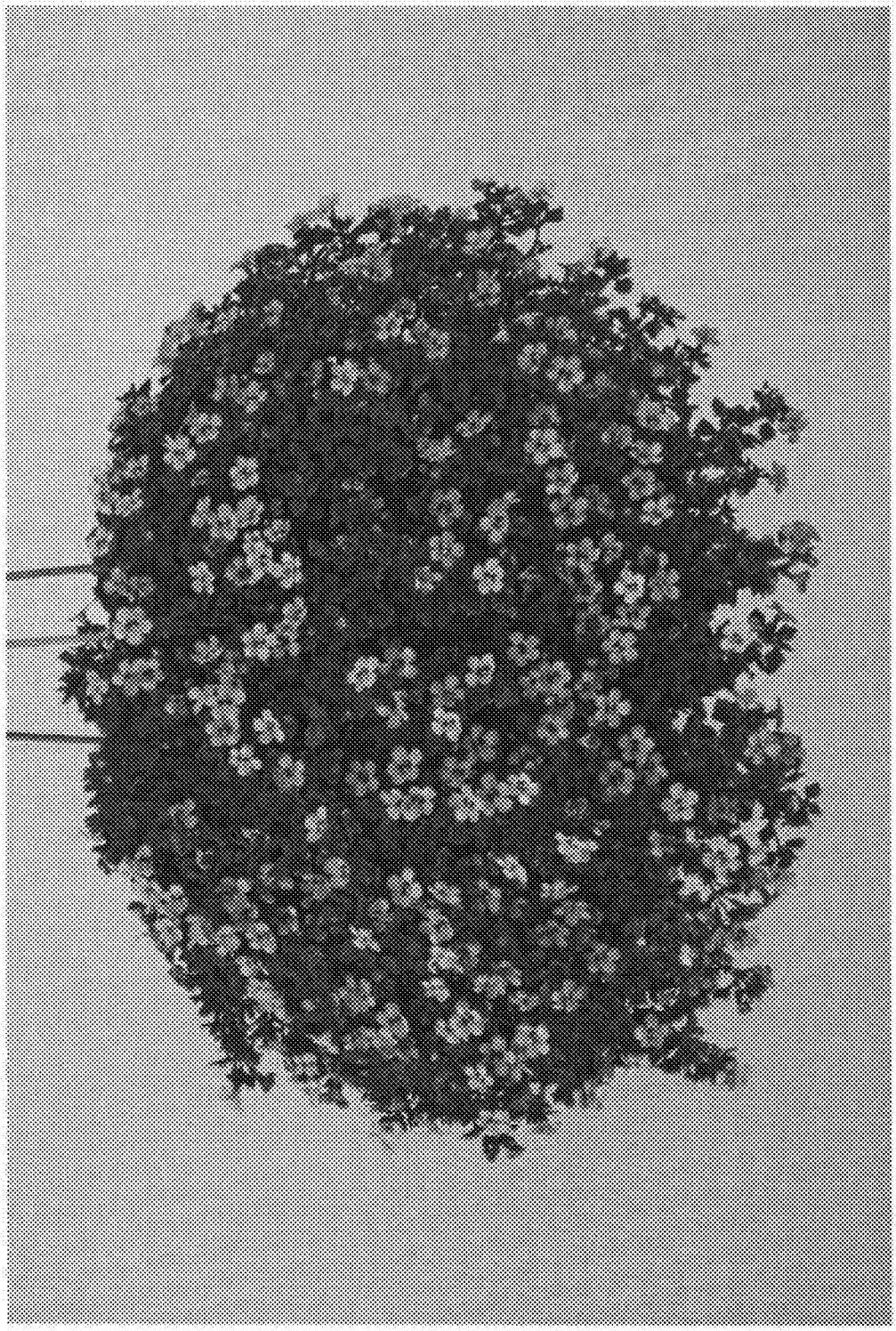

The accompanying photograph in FIG. 1 illustrates in full color a typical plant of 'DANCOP29' grown in a greenhouse, in a 13 cm pot. Age of the plant photographed is approximately 3 months from a rooted cutting.

Figure 2:
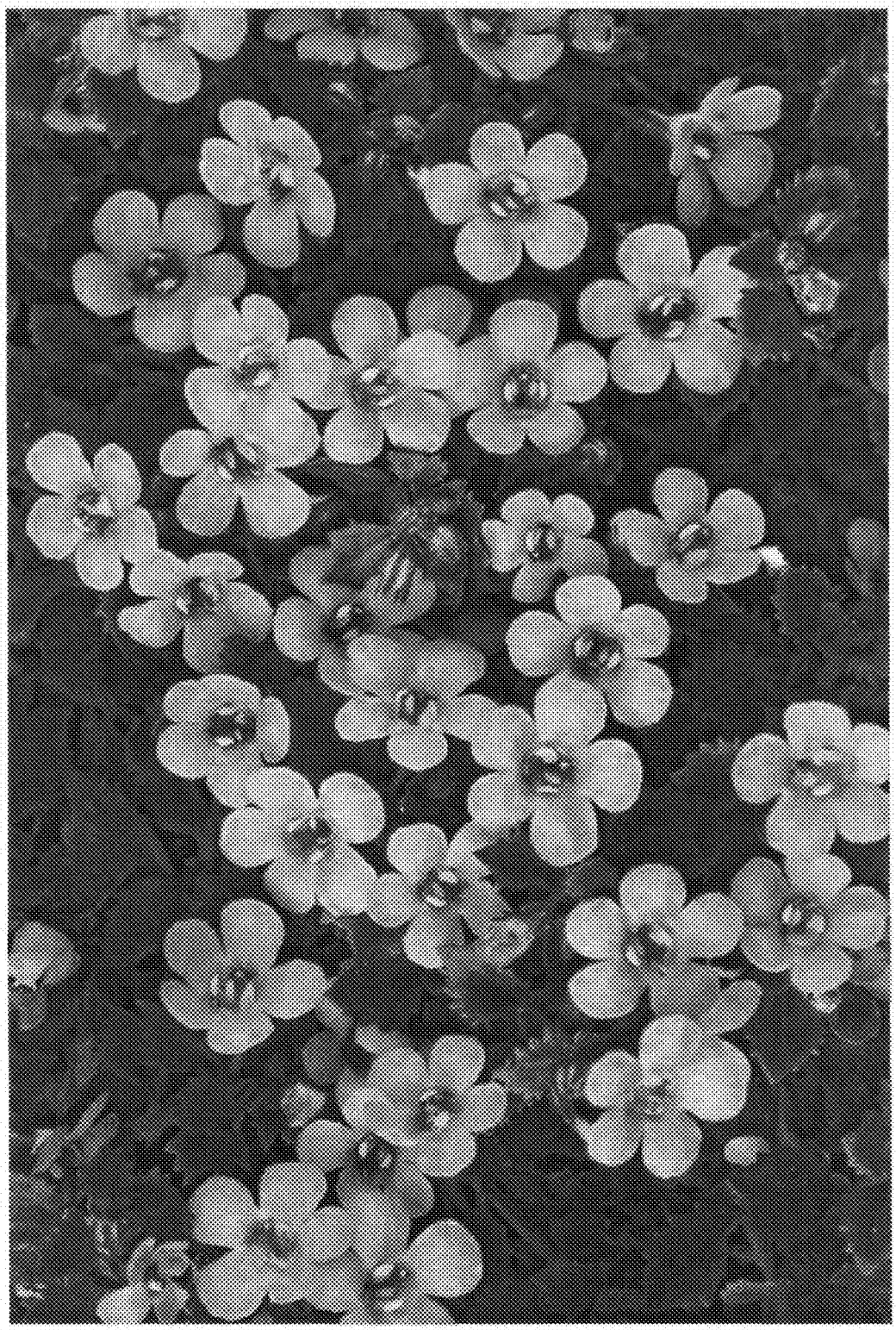

FIG. 2 illustrates in full color a close up of a typical bloom of 'DANCOP29.' The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used.

The following observations and measurements describe 'DANCOP29' plants grown in a greenhouse in Moshav Mishmar Hashiva, Israel. The growing temperature ranged from 15° C. to 24° C. during the day and 13 to 15° C. at night. The greenhouse is un-shaded, giving bright, normal sunlight conditions. Measurements and numerical values represent averages of typical plant types.

Botanical classification: *Sutera cordata* 'DANCOP29'.

PROPAGATION

Time to initiate roots: About 7 days at approximately 20° C.

Root description: Fine, densely fibrous.

PLANT

Growth Habit: Trailing.

Pot size of plant described: 13 cm.

Height: Approximately 7 cm.

Plant spread: Approximately 55 cm.

Growth rate: Medium.

Branching characteristics: Very well branched.

Length of lateral branches: Approximately 60 cm.

Diameter of lateral branches: Approximately 0.3 cm.

Quantity of lateral branches: Approximately 8.

Characteristics of primary lateral branches:

- *Form.*—Cylindrical.
- *Diameter.*—About 0.3 cm.
- *Color.*—Near RHS Yellow-Green 146B.
- *Texture.*—Velvety.
- *Strength.*—Strong.

Internode length: About 2.5 cm.

Age of plant described: Approximately 90 days from a rooted cutting.

FOLIAGE

Leaf:

- *Arrangement.*—Opposite.
- *Quantity.*—Approximately 300 per primary branch.
- *Average length:* 2.5 cm.
- *Average width.*—2 cm.
- *Shape of blade.*—Ovate.
- *Apex.*—Acute.
- *Base.*—Acuminate.
- *Margin.*—Serrate.
- *Texture of top surface.*—Velvety.
- *Pubescence.*—Slight.
- *Aspect.*—Slanted upward.
- *Color.*—Young leaves: Upper surface: Near RHS Green 137A. Lower surface: Near RHS Green 137B. Mature leaves: Upper surface: Near RHS Green 147A. Lower surface: Near RHS Green 147B.

Veins:

- *Venation pattern.*—Pinnate.
- *Color.*—Upper surface: Near RHS Green 147A. Lower surface: Near RHS Green 147B.

Petiole: Length: Approximately 0.6 cm. Diameter: Approximately 0.2 cm. Color: Near RHS Green 147A. Texture: Velvety.

FLOWER

Natural flowering season: Continuously Spring through Autumn. In moderate climates Winter flowering as well.

Days to flowering from rooted cutting: About four weeks.

Inflorescence and flower type and habit: Inflorescence is solitary, axillary, salverform.

Rate of flower opening: 1 to 2 days from bud to fully opened flower.

Flower Longevity on plant: About 7 days.

Persistent or self-cleaning: Persistent.

Bud:

- *Shape.*—Spatulate.
- *Length.*—About 1.2 cm.
- *Diameter.*—About 0.5 cm.
- *Color.*—Near RHS Violet-Blue 92A.

Flower size:

- *Diameter.*—About 2.3 cm.
- *Length.*—About 1.1 cm.
- *Corolla tube diameter.*—About 0.3 cm.
- *Corolla tube length.*—About 0.7 cm.

Corolla/petals:

- *Arrangement.*—Gameopetalous.
- *Lobe length.*—About 0.7 cm.
- *Lobe width.*—About 0.7 cm.
- *Quantity.*—5.
- *Texture.*—Velvety.
- *Lobe apex.*—Rounded.
- *Lobe shape.*—Rounded.
- *Margin.*—Entire.
- *Aspect.*—Flat, right angle to the flower tube.
- *Color.*—When opening: Upper surface: Near RHS Violet N 88B. Lower surface: Near RHS Violet N 88C. Fully opened: Upper surface: Near RHS Violet N 88C. Lower surface: Near RHS Violet N 88D. Inner corolla tube color: Near RHS Yellow-Orange 17A. Outer corolla tube color: Near RHS Violet N 88D.

Calyx/sepals:

- *Quantity per flower.*—5.
- *Shape.*—Linear.
- *Length.*—About 0.7 cm.
- *Width.*—About 0.1 cm.
- *Apex.*—Acute.
- *Base.*—Fused.
- *Margin.*—Entire.
- *Texture.*—Upper surface: Velvety. Lower surface: Velvety.
- *Color.*—Upper surface: Near RHS Yellow-Green 144A. Lower Surface: Near RHS Yellow-Green 144A.

Peduncle: None.

Pedicel:

- *Length.*—Approximately 0.8 cm.
- *Diameter.*—Approximately 0.1 cm. Color: Near RHS Yellow-Green 146B.
- *Orientation.*—Slanted upward.
- *Pubescence.*—Slight pubescence.

Fragrance: None.

REPRODUCTIVE ORGANS

Stamens:

- *Number.*—4.
- *Filament length.*—Approximately 0.8 cm.
- *Filament color.*—Near RHS Yellow-Green 154C.

Anthers: Shape: Cylinder. Length: Approximately 0.1 cm. Color: Near RHS Yellow-Orange 14A. Pollen: Color: RHS Yellow-Orange 14A. Quantity: Moderate amount.

Pistil:

- *Number.*—1.
- *Length.*—About 1 cm.

*Styles.*—Length: About 0.8 cm. Color: Near RHS Yellow-Green 144C.

*Stigma.*—Shape: Linear, undulating. Color: Near RHS Yellow-Green 144A. Ovary Color: Near RHS Green 146B.

OTHER CHARACTERISTICS

Seeds and fruits: The fruit is an ellipsoid capsule, containing about 20 rounded, light brown seeds, Near RHS Grey-Brown 199C, of about 0.5 mm in size.

Disease resistance: Neither resistance nor susceptibility observed.

Temperature tolerance: The new variety tolerates temperatures between 5 to 35° C.

What is claimed is:

1. A new and distinct cultivar of *Sutera* plant named 'DANCOP29' as herein illustrated and described.

* * * * *